(12) United States Patent
Fremming et al.

(10) Patent No.: US 7,896,818 B2
(45) Date of Patent: Mar. 1, 2011

(54) SAMPLER CAP

(75) Inventors: Niels Fremming, Herlev (DK); Jørgen Andersen, Herlev (DK)

(73) Assignee: Radiometer Medical ApS, Bronshoj (DK)

( * ) Notice: Subject to any disclaimer, the term of this patent is extended or adjusted under 35 U.S.C. 154(b) by 2175 days.

(21) Appl. No.: 10/465,894

(22) Filed: Jun. 20, 2003

(65) Prior Publication Data

US 2003/0236497 A1    Dec. 25, 2003

(30) Foreign Application Priority Data

Jun. 25, 2002    (DK) ............................... 2002 00974

(51) Int. Cl.
*A61B 5/00* (2006.01)
(52) U.S. Cl. .................................................... 600/573
(58) Field of Classification Search ......... 600/573–580; 604/533, 126, 247, 190
See application file for complete search history.

(56) References Cited

U.S. PATENT DOCUMENTS

| | | | | |
|---|---|---|---|---|
| 584,091 | A * | 6/1897 | Leidich ..................... | 137/849 |
| 4,244,378 | A * | 1/1981 | Brignola ..................... | 600/579 |
| 4,263,922 | A * | 4/1981 | White ..................... | 600/576 |
| 4,327,746 | A | 5/1982 | Feaster | |
| 4,378,812 | A | 4/1983 | Sarstedt | |
| 4,459,139 | A * | 7/1984 | vonReis et al. ................... | 96/6 |
| 5,086,783 | A * | 2/1992 | Macors et al. ............... | 600/578 |
| 5,125,415 | A | 6/1992 | Bell ........................... | 128/766 |
| 5,313,969 | A * | 5/1994 | Hsieh ........................ | 600/577 |
| 5,624,402 | A | 4/1997 | Imbert ....................... | 604/111 |
| 5,843,046 | A * | 12/1998 | Motisi et al. ................ | 604/256 |
| 6,135,172 | A | 10/2000 | Fere et al. | |
| 6,155,991 | A * | 12/2000 | Beat et al. .................... | 600/573 |

FOREIGN PATENT DOCUMENTS

| | | |
|---|---|---|
| DE | 29 08 817 | 9/1980 |
| DE | 37 40 269 A1 | 6/1989 |
| EP | 0 071 329 A1 | 2/1983 |
| EP | 0 321 032 | 6/1989 |
| EP | 0 378 353 | 7/1990 |
| EP | 0 396 016 | 11/1990 |
| EP | 1 103 304 | 5/2001 |
| JP | 55-125849 | 9/1980 |
| JP | 56-91734 | 7/1981 |
| JP | 2-4337 | 1/1990 |
| JP | 3-63570 | 3/1991 |
| JP | 3-197864 | 8/1991 |
| JP | 2001-507134 | 5/2001 |
| JP | 2001-235478 | 8/2001 |

* cited by examiner

*Primary Examiner*—Nicholas D Lucchesi
*Assistant Examiner*—Theodore J Stigell
(74) *Attorney, Agent, or Firm*—Morgan, Lewis, Bockius LLP

(57) ABSTRACT

A sampler cap includes a sampler connector, an analyzer connector and a liquid impermeable closure member, which may be a membrane or a filter. The sampler cap may be used to transfer a test sample to an analyzer without removing the sampler cap from the sampler.

3 Claims, 8 Drawing Sheets

SAMPLER CAP

BACKGROUND OF THE INVENTION

1. Field of the Invention

The present invention relates to a sampler cap.

2. Discussion of the Related Art

Proper handling of a blood sample during the preanalytical phase of blood analysis is essential in order to obtain correct information on the patient's condition. During the preanalytical phase, a blood sample may coagulate, settle, react with air included in the blood sampler or exchange gas with the surroundings. All of these phenomena may bias the result of the analysis and should be avoided.

In particular for the analysis of blood gasses, any air introduced into the blood sampler and any gas exchange may bias the result of the analysis. Incorrect and misleading values may be worse for the patient than no values at all, and thus any air should be removed from the sampler and any gas exchange with the surroundings should be avoided.

Gas exchange with the surroundings may be avoided by closing the sampler. For example a syringe with a tip may be closed with a sampler cap. Such closing sampler caps are known in the prior art.

U.S. Pat. No. 5,624,402 discloses a cap for closing a syringe tip by sealing engagement with the tip of the syringe.

Air in a syringe holding a blood sample may be removed by covering the tip of the syringe by a piece of gauze, and subsequently expelling the air while holding the syringe with the tip in an upright position. This technique, however, poses a risk of the operator contacting hazardous blood samples.

Alternatively, the tip of the syringe may be provided with a sampler cap, which allows passage of air, and the sample in the syringe may be vented by means of such cap. Upon depressing the syringe plunger air may be expelled from the syringe via a venting mechanism in the cap while blood is retained by the venting mechanism. Such sampler caps are known in the prior art.

U.S. Pat. No. 5,125,415 discloses a cap in which the venting mechanism comprises a hydrophilic filter. The hydrophilic filter, e.g. a porous polypropylene impregnated with cellulose, is permeable to air under dry conditions, whereas it expands and seals the cap when exposed to blood.

The sampler caps of the prior art suffer from the disadvantage that they must be removed from the tip of the syringe prior to transfer of a test sample from the syringe to an analyzer. Accordingly, during the cap removal step as well as during the transfer step the operator is facing the risk of exposure to the blood sample.

Thus, despite the hitherto proposed sampler caps, there is still a need for a cap that needs not be removed from a sampler prior to transfer of a test sample to the analyzer.

SUMMARY OF THE INVENTION

This has been achieved by a sampler cap according to a first exemplary embodiment of the present invention, comprising a hollow body providing a sampler connector and an analyzer connector, and a liquid impermeable closure member intersecting the hollow body between the sampler connector and the analyzer connector.

As used herein, the term "sampler" comprises a syringe, a capillary tube and a test tube, e.g. a vacuum test tube, for sample collection as well as for any other intended use.

Thus, as also used herein, the term "sampler cap" means a cap to be connected to the open end of a sampler, e.g. to the tip of a syringe or to the open end of a capillary tube or a test tube.

As used herein, the term "sampler connector" means the part of the cap that engages the sampler. Likewise, as used herein, the term "analyzer connector" means the part of the cap that engages an analyzer.

As further used herein, the term "liquid impermeable closure member" means a structure that is impermeable to liquid and that closes the hollow body of the cap against any transport of liquid. The liquid impermeable closure member may be impermeable to gasses as well, thus completely sealing the sampler against fluid transport, or it may be permeable to gasses.

The sampler connector of the sampler cap engages with the sampler and forms a closed connection thereto. When connected to a syringe the sampler connector may be applied to the syringe tip (referred to as the syringe luer), and the sampler connector may be applied to the body of the capillary tube when connected to a capillary tube. When connected to a test tube, e.g. a vacuum test tube, the sampler connector may be connected to a plug of the test tube or it may be fitted onto or into the body of the test tube.

In order to provide the closed connection to the sampler, the sampler connector may have seals, e.g. rubber O-rings, to provide airtight connection to the sampler.

In order for the sampler cap not to accidentally fall off the sampler, the sampler connector may have locking means, e.g. a screw coupling, a bayonet joint or a snap lock coupling. For connection to a syringe the locking means may be a luer lock.

According to this first exemplary embodiment of the invention, wherein the sampler has a cap with an analyzer connector, a test sample is transferred from a sampler to an analyzer by (a) bringing the sampler with the cap into fluid communication with the analyzer by connecting the analyzer connector to an inlet of the analyzer, (b) entering an inlet probe of the analyzer into the sampler through the cap, (c) collecting the test sample from the sampler through the inlet probe, and (d) retracting the inlet probe from the sampler.

Thus, upon entering the analyzer inlet probe into the sampler cap, the closure member is penetrated by the inlet probe, preferably upon application of a penetration force of a few Newtons.

According to a preferred embodiment of the invention, the liquid impermeable closure member comprises a membrane.

As used herein, the term "membrane" means a non-porous structure, which is impermeable to gasses and liquids.

The membrane may be made from any material which allows inlet probe penetration and which is impermeable to gasses and liquids. Preferably, the membrane is made from a silicone rubber.

According to another preferred embodiment of the invention, the liquid impermeable closure member comprises a filter.

As used herein the term "filter" means a porous structure which is permeable to gasses, but which is impermeable to liquids. The filter allows air passage when expelling of air from the sampler and has a pore cross section diameter in the range 0.2-2 μm, preferably about 0.3 μm.

The filter may have predominantly hydrophobic characteristics or predominantly hydrophilic characteristics.

A filter with hydrophobic characteristics may be a filter made from a hydrophobic material like polyethylene, polypropylene or polytetrafluoroethylene. Alternatively, the filter may have a surface, which is modified by a hydrophobic material like silicone, e.g. it may be a cellulose or glass filter with silicone coated filter threads. The filter is permeable to gasses while aqueous phases are restricted from penetration into the porous structure of the filter due to the hydrophobic character thereof.

A filter with hydrophilic characteristics may be a filter made from a material like cellulose or a cellulose derivative like carboxymethylcellulose. Such materials swell when exposed to aqueous phases, thereby blocking the porous structure of the filter. When dry, the porous structure is permeable to gaseous phases.

It should be understood, that the closure member may have a combined membrane-filter structure, e.g. part of the closure member having membrane characteristics, i.e. being impermeable to gasses and liquids and part of the closure member having filter characteristics, i.e. being permeable to gasses, but impermeable to liquids. The combined structure may be e.g. a layered structure or a structure with a radial distribution of areas with membrane and filter characteristics, respectively.

In order to facilitate inlet probe penetration, the closure member preferably has a weakening zone. The application of a weakening zone reduces the force required for penetration and reduces the risk of spills and damage to the inlet probe and sampler as caused by sudden penetration of the closure member. The weakening zone may be at the center of the closure member.

The weakening zone may be provided in any way, which reduces the closure member tensile strength. For example, the weakening zone may be provided as a closure member zone of reduced thickness or a closure member zone with pinholes.

Preferably, the weakening zone in the closure member is a longitudinal slit, which may pass entirely through the closure member or only partially through the closure member.

Penetration of the weakening zone by the inlet probe preferably provides an air passage which allows an air flow to equilibrate any pressure differences across the closure member, e.g. as created during collection of a test sample from the sampler. Accordingly, the longitudinal slit in the closure member preferably may be longer than the diameter of the inlet probe to provide the air passage adjacent to the penetration spot of the inlet probe.

According to a second exemplary embodiment of the invention, a sampler cap is provided which comprises a hollow body providing a sampler connector having a first open end and a second end, and a liquid impermeable closure member closing the second end of the sampler connector, the closure member being a filter and having a weakening zone.

According to this second exemplary embodiment of the invention, in which a sampler has a cap, a test sample is transferred from a sampler to an analyzer by (a) bringing the sampler with the cap into fluid communication with the analyzer by approaching the cap to an inlet of the analyzer, (b) entering an inlet probe of the analyzer into the sampler through the cap, (c) collecting the test sample from the sampler through the inlet probe, and (d) retracting the inlet probe from the sampler.

Thus, the sampler cap according to the first as well as to the second exemplary embodiment of the invention allows transfer of a test sample to an analyzer without the sampler cap being removed from the sampler.

Preferably, the sample contained in the sampler is vented via the cap prior to collecting the test sample.

Thus, according to a preferred embodiment of the invention the sampler cap comprises a venting conduit allowing air to pass from the sampler connector to the surroundings.

As used herein, the term "venting conduit" means any combination of channels, cavities, chambers and/or other structural elements provided within the sampler cap, which form a continuous extending pathway to the surroundings. Any inlet and outlet openings of the venting conduit are part thereof.

In the case of the closure member being a membrane, the venting conduit provides a pathway for air to be expelled from the sampler to the surroundings during a venting operation. In the case of the closure member being a filter, the venting conduit provides a pathway for air to be expelled from the sampler to the surroundings subsequent to any preceding venting operation, during which the filter may have been blocked.

The venting conduit preferably comprises an inlet located adjacent to the closure member. During the venting operation, the sampler with the sampler cap is preferably held in an upright position. Thus, upon providing the inlet of the venting conduit adjacent to the closure member, air bubbles to be expelled from the sampler will gather at the venting conduit inlet and thus be arranged for expelling.

The inlet of the venting conduit may preferably open into a passage. The passage may be permanently open or it may be formed when a positive pressure is exerted on the sampler connector side of the closure member.

According to this exemplary embodiment of the invention, the closure member is preferably flexible. Thus, upon exercise of the positive pressure in the sampler during venting, the closure member may deflect in the direction opposite the sampler connector, forming the passage into which the inlet of the venting conduit opens.

The term "a positive pressure" refers to the pressure as applied during intended operation of the sampler with the sampler cap. Thus, the term "a positive pressure" should be understood as an overpressure in the range 0-1 bar, e.g. as created when operating the plunger of a 1 $cm^2$ cross section syringe with a force in the range of 0-10N, to gently expel air and foam from the sampler.

According to a preferred embodiment, the venting conduit comprises a venting chamber into which the passage opens. This venting chamber is adapted to accommodate any foam or excessive sample from the sampler expelled during the venting operation.

The venting chamber preferably has one or more narrowings dividing the venting chamber into two or more subchambers. The combination of the passage, the one or more narrowings and the subchambers serves to reduce sample foaming during venting.

The venting conduit preferably comprises a liquid impermeable filter to prevent any blood from escaping from the venting conduit while allowing passage of air. The liquid impermeable filter may be positioned anywhere in the venting conduit. Preferably, the liquid impermeable filter is positioned in one of the narrowings of the venting conduit. The liquid impermeable filter preferably is made from the same materials and preferably has the same pore dimensions as the previously mentioned filter.

According to a preferred embodiment of the invention, the closure member closes the venting conduit when an excessive pressure is exerted on the sampler connector side of the closure member. This is accomplished as the closure member is deflected in the direction opposite the sampler connector and seals against a structural element of the sampler cap. Although in such case the sample may penetrate the venting conduit even beyond the liquid impermeable filter, it is blocked when the closure member seals against the structural element. The closure member may have a hydrophobic outer layer, e.g. of silicone, to improve sealing against the structural element.

The term "an excessive pressure" refers to the pressure as applied during unintended, abusive or accidental high pressure operation of the sampler with the sampler cap. Thus, the term "an excessive pressure" should be understood as an overpressure in the range 1-10 bar, e.g. as created when operating the plunger of a 1 cm$^2$ cross section syringe with a excessive force in the range of 10-100N.

The sampler cap preferably comprises a collection chamber for collecting displaced sample, the collection chamber having an inlet located adjacent the closure member opposite the sampler connector.

As used herein, the term "displaced sample" means any sample from the sampler which is displaced therefrom, including sample displaced during venting and when the inlet probe enters into the sampler cap and the sampler.

Insertion of the inlet probe into the sampler displaces a sample volume corresponding to the volume of the part of the inlet probe that is extended into the liquid phase in the sampler. Such displaced sample may escape through the passage in the closure member formed during inlet probe penetration. In order to prevent this sample volume from being spilled from the sampler cap, it is collected in the collection chamber, the inlet of which is located adjacent the closure member opposite the sampler connector. Thus, displaced sample is led into the collection chamber, preferably by means of capillary forces. Upon inlet probe retraction, the flow may be reversed and displaced sample may be returned to the sampler.

Preferably the collection chamber is partly formed by the structural element.

According to another preferred embodiment of the invention, the collection chamber is part of the venting conduit, e.g. the collection chamber and the venting chamber being one and the same chamber. Thus, the collection chamber may collect any sample that by accident escapes from a liquid impermeable filter in the venting conduit.

Any of the collection chamber and the venting conduit subchambers may comprise an absorbing material to retain sample.

Any of the collection chamber and the venting conduit subchambers may be provided with a structure comprising a pattern of capillary lamellas or fins. The capillary lamellas or fins may retain sample and ease the assembly of the sampler cap.

In case samples need not be vented prior to transfer from a sampler to an analyzer, a different sampler cap may be used. Thus, according to a third exemplary embodiment of the invention a sampler cap is provided which comprises a hollow body providing a sampler connector and an analyzer connector.

Thus, the sampler cap according to the first, second and third exemplary embodiment of the invention allows transfer of a test sample to an analyzer without the sampler cap being removed from the sampler.

The connection between the analyzer connector and the analyzer preferably allows equilibration of any pressure differences created during collection of test samples and thus preferably allows passage of air. Accordingly, the analyzer connector preferably comprises air passage means. The analyzer connector air passage means may be provided, for example, as ribs on the inside of the bore of the analyzer connector, providing passage between the analyzer connector and the analyzer inlet. As another alternative, the air passage means may be provided as a perforation in the analyzer connector wall.

In order for the sampler cap not to accidentally fall off the analyzer inlet, the analyzer connector may have locking means, e.g. a screw coupling, a bayonet joint or a snap lock coupling on the inside or the outside of the analyzer connector. It may as well have a projection or indentation onto or into which a holdfast of the analyzer inlet can be secured.

The sampler cap may be provided as a separate component or as an assembly with the sampler. Thus, the invention further covers an assembly comprising a sampler and a cap according to the invention and having a first end with a sampler connector and a second end, wherein the first end with the sampler connector is connectable to the sampler.

According to a preferred embodiment of the invention, the assembly further comprises a double-ended needle, wherein one end of the double-ended needle is receivable by the second end of the sampler cap. According to this embodiment of the invention, the assembly comprises a sampler cap with a first end having a sampler connector and a second end, a sampler connected to the sampler connector of the sampler cap and a double ended needle connected to the second end of the sampler cap.

In a preferred embodiment of this assembly, the sampler is a syringe. Such assembly is particularly useful for collection of a blood sample from a patient. When collecting a sample, the sampler is equipped with a sampler cap with a membrane as closure member, and a vacuum is created in the sampler by retracting the plunger of the sampler. An artery or a vein, preferably a vein, of the patient is punctured by one end of the double ended needle, and subsequently the other end of the double-ended needle is connected to the sampler via the sampler cap, penetrating the closure member thereof. Due to the vacuum in the sampler, blood from the patient now flows into the sampler. Upon completion of the sample collection, the sampler with the sample cap is disconnected from the double-ended needle, and the sample held in the sampler may be vented. If appropriate, additional samplers may be filled upon repeating the procedure.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the following preferred embodiments of the invention are described with reference to the drawings in which.

DETAILED DESCRIPTION OF THE PREFERRED EMBODIMENTS

Reference will now be made in detail to the preferred embodiments of the present invention, examples of which are illustrated in the accompanying drawings.

Figure 1:
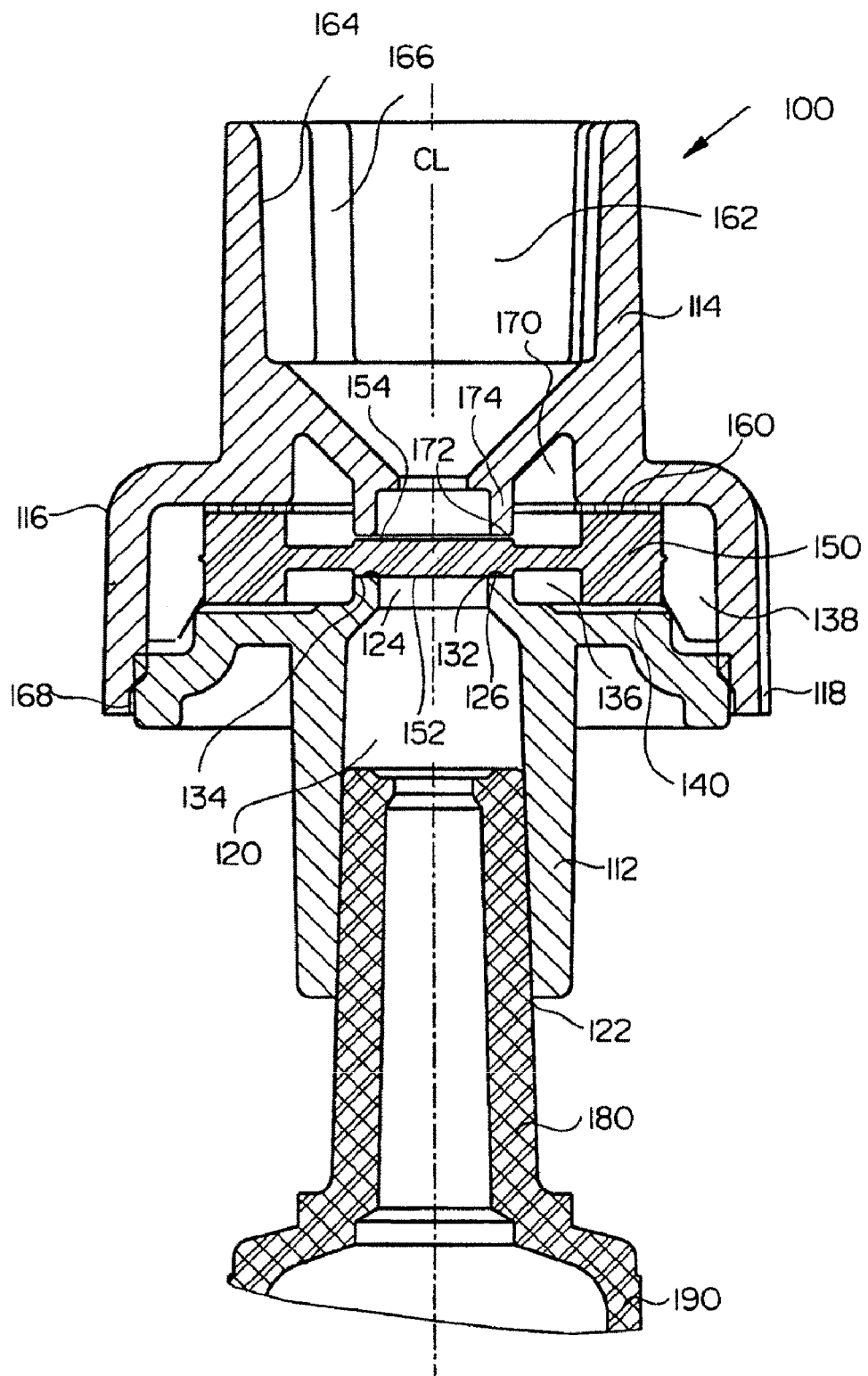
FIG. 1 is a sectional view of a sampler cap for a syringe.

FIG. 1 shows a sampler cap 100 for use, for example, with a blood sampling syringe.

The sampler cap 100 comprises a hollow body. The hollow body is a two part body with a first part 112 comprising a sampler connector 120 and a second part 114 comprising an analyzer connector 162. The two parts of the body may be made from polystyrene and may be ultra sound-welded at the welding zone 168.

The sampler connector 120 has a first open end 122 and a second end 124. A syringe luer 180 of a syringe 190 fits into the sampler connector 120, as shown in FIG. 1.

The analyzer connector 162 fits onto an analyzer inlet.

The sampler cap 100 has a venting conduit comprising an inlet 132, a first subchamber 136 and a second subchamber 138, separated by a narrowing in terms of a set of capillary channels 140, a liquid impermeable filter 160, a collection chamber 170 for collecting displaced sample, and a chamber inlet 172. The venting conduit extends from the sample connector 120 to the analyzer connector 162.

The liquid impermeable filter 160 may be porous and made from poly tetrafluoroethylene, for example. In order to efficiently retain blood cells of the blood sample, the pore cross section diameter of the filter is 0.3 μm.

The sampler cap has a membrane 150. The membrane 150 closes the second end 124 of the sample connector 120 at the inlet 132 of the venting conduit. When exerting a positive pressure of e.g. 0.2 bar on the sampler connector side 152 of the membrane 150 a passage 134 is formed between the membrane 150 and the sampler connector 120. At the position of the passage 134 the sampler connector 120 has a bead 126 to close the sampler connector 120 when no positive pressure is exerted on the sampler connector side 152 of the membrane 150.

The membrane 150 may be made from silicone rubber. The membrane 150 has a longitudinal through-cut (not shown) at its center to facilitate inlet probe penetration.

The inlet 172 of the collection chamber 170 is located at the analyzer connector side 154 of the membrane 150 and is formed between a structural element 174 of the hollow body and the membrane 150. When an excessive pressure of e.g. 5 bars is exerted on the sampler connector side 152 of the membrane 150, the membrane 150 deflects to seal against the structural element 174 and thus closes the inlet 172 and the venting conduit.

If a subambient pressure is applied on the sampler connector side 152 of the membrane 150, e.g. by accidentally pulling back a plunger (not shown) of the syringe 190, the membrane 150 deflects towards the sampler connector 120 to firmly close the passage 134 and seal the inlet 132. In this way back-flow of blood from the sampler cap 100 to the syringe 190 is prevented.

The inlet 132 of the venting conduit and the inlet 172 of the collection chamber 170 are located symmetrically on the sampler connector side 152 of the membrane 150 and on the analyzer connector side 154 of the membrane, respectively. In this way venting and closing of the sampler cap 100 is optimized.

The analyzer connector 162 has an inner surface 164 with has three longitudinal ribs 166 which have a two-fold purpose: The ribs 166 fit firmly onto the analyzer inlet and they allow air flow into the sampler cap 100 during collection of a test sample.

On the outer surface 116 of the hollow body are fins 118 preventing the sampler cap 100 with the syringe 190 from rolling when placed on table.

In operation, the sampler cap 100 is placed on the syringe luer 180 to close the syringe 190.

The syringe 190 is vented by activating the syringe plunger (not shown) to expel air from the syringe 190, through the venting conduit.

A flow of blood foam may follow the air flow. The combination of the passage 134, the first subchamber 136, the set of capillary channels 140 and the second subchamber 138 reduces the foaming, which is minimized when the blood foam front reaches the liquid impermeable filter 160. The blood foam flow is stopped at the filter 160.

A flow of blood may follow the blood foam flow. The blood is also stopped at the liquid impermeable filter 160, and excessive blood volume may be accommodated in the subchambers 136 and 138.

The sampler cap 100 with the syringe 190 is subsequently connected to the analyzer inlet by means of the analyzer connector 162.

Figure 8:
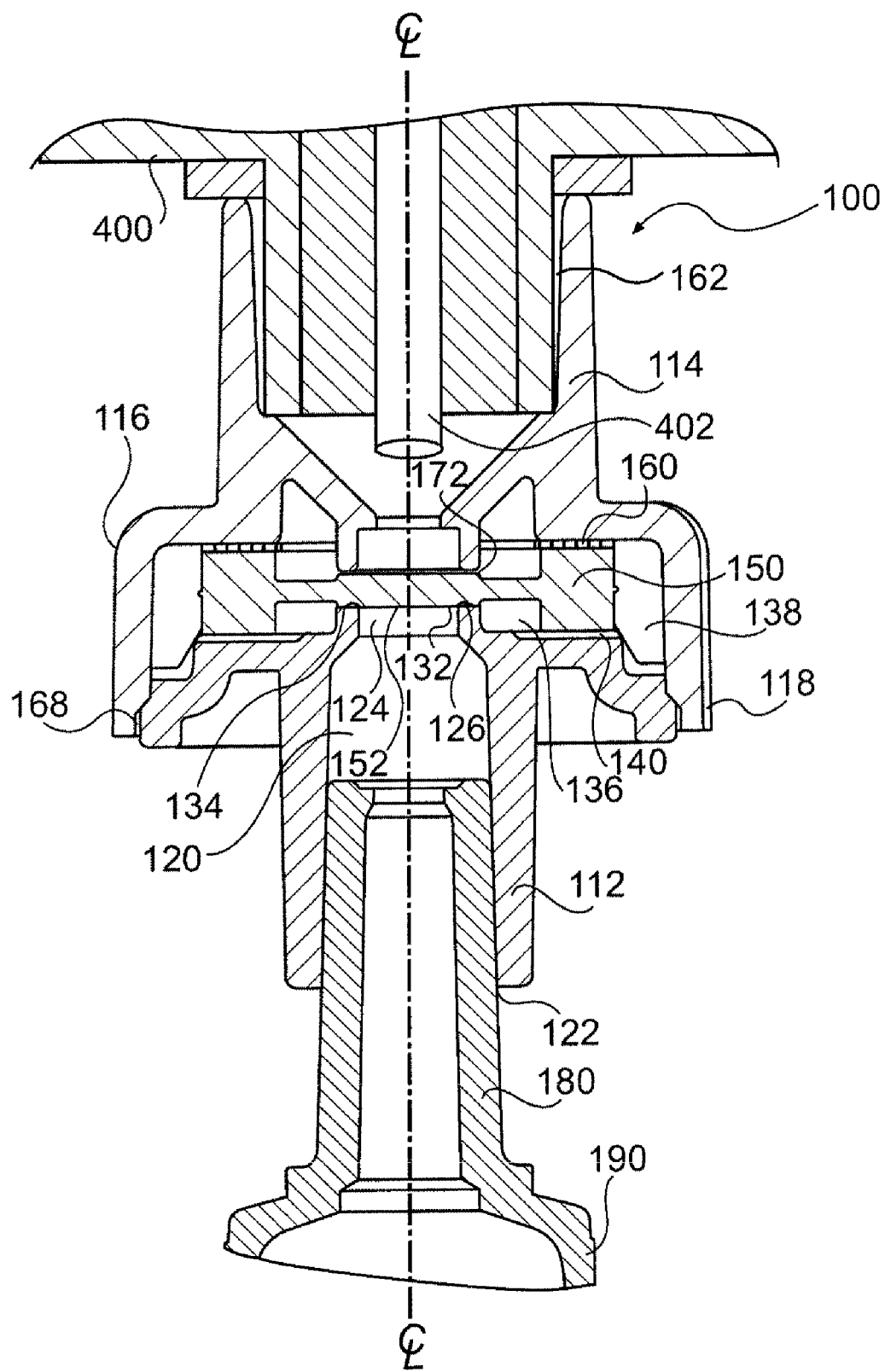
FIG. 8 is a sectional view of the cap of FIG. 1 with an inlet probe entered into it.

As shown in FIG. 8, the analyzer inlet probe 402 is approached to the membrane 150 to penetrate the membrane 150 at the longitudinal through-cut (not shown) and to enter into the syringe 190. The inlet probe 402 preferably enters the sampler cap 100 and syringe 190 along the center line CL.

Blood displaced to the analyzer connector side 154 of the membrane 150 via the longitudinal through-cut (not shown) in the membrane during the inlet probe penetration is collected in collection chamber 170. Upon collection of a test sample, the flow may be reversed, or compensatory air is allowed to flow into the syringe 190 via the longitudinal through-cut (not shown).

Upon withdrawal of the inlet probe 402 the longitudinal through-cut in the membrane 150 seals to provide a bubble point of approx. 0.01 bar.

Figure 2:
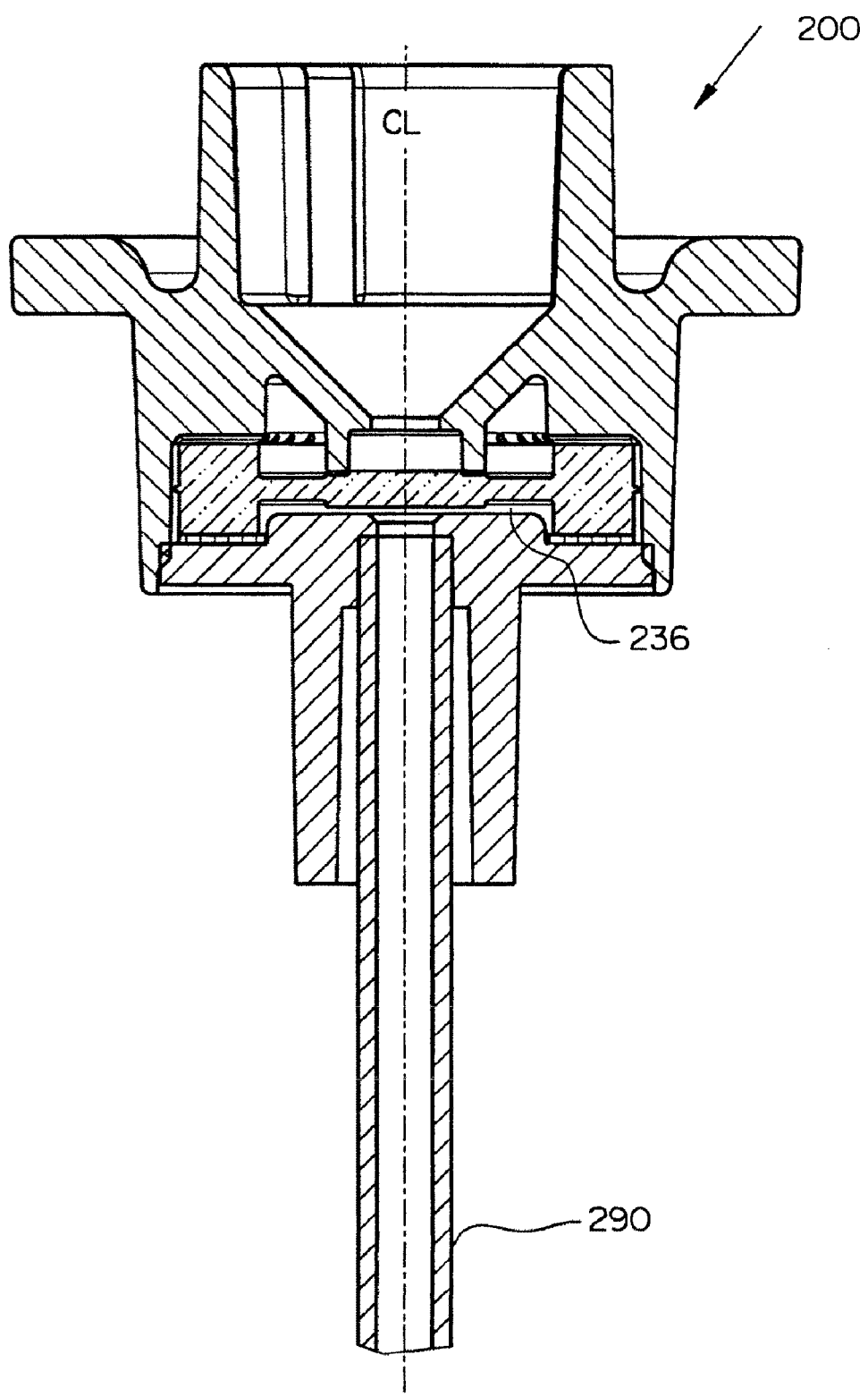
FIG. 2 is a sectional view of a sampler cap for a capillary tube.

FIG. 2 shows a sampler cap 200 for use, for example, with a capillary tube.

Compared to the sampler cap 100, the sampler cap 200 is miniaturized to fit the smaller capillary tube 290. In particular, the subchamber 236 is miniaturized as only a very small volume of blood is expelled from the capillary tube 290 during venting.

Compared to the operation of the sample cap 100 with a syringe, the operation the sampler cap 200 with a capillary tube 290 is slightly different in that the venting is done during collection of the sample from the patient. Thus, blood sample is forced into the capillary tube 290 by capillary action, simultaneously venting the capillary tube 290.

Figure 3:
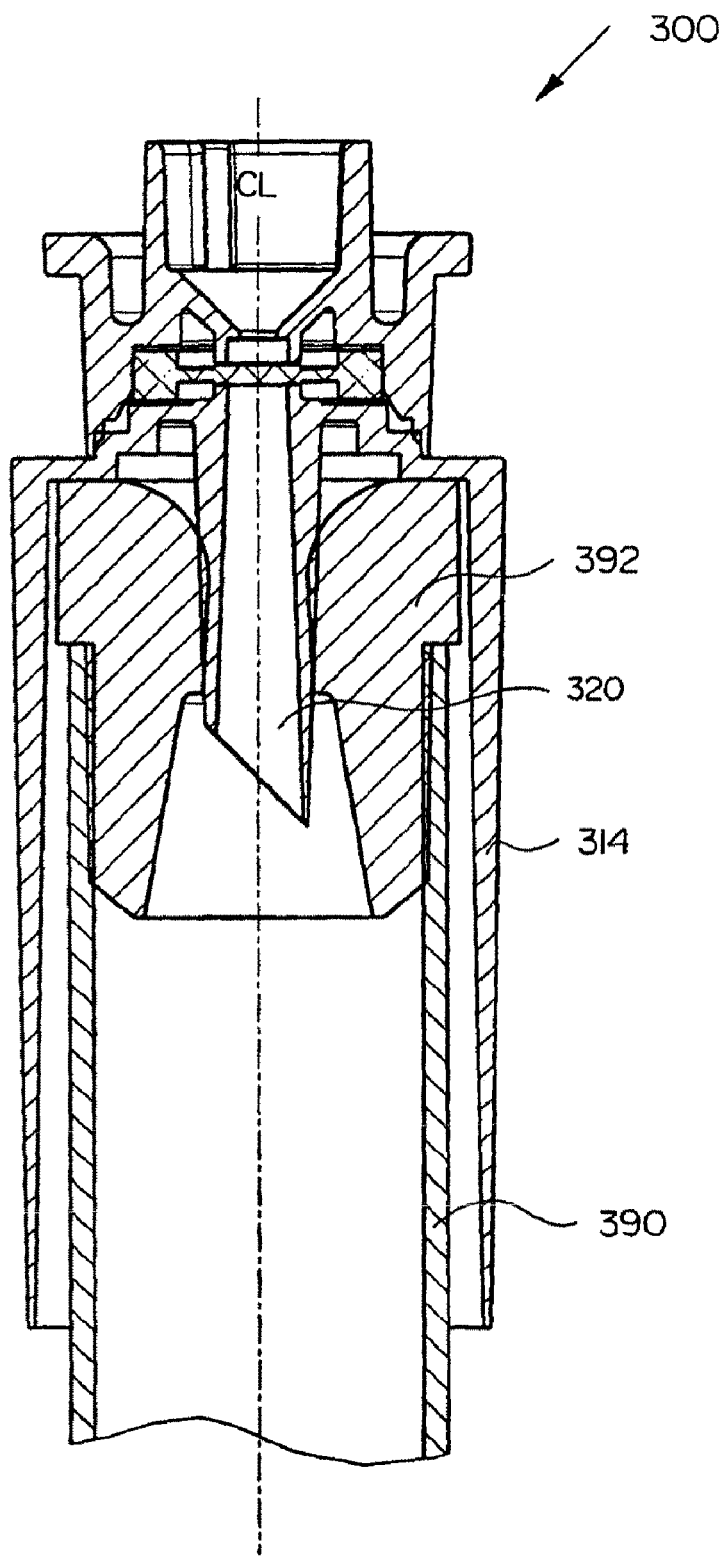
FIG. 3 is a sectional view of a sampler cap for a vacuum test tube.

FIG. 3 shows a sampler cap 300 for use, for example, with a vacuum test tube.

Compared to the sampler cap 100, the sampler cap 300 has a pointed sampler connector 320 to penetrate a plug 392 of vacuum test tube 390.

Compared to the operation of the sample cap 100 for a syringe, the operation the sampler cap 300 for a vacuum test tube 390 is simplified in that there is no venting step.

The sampler cap 300 for a vacuum test tube 390 has a skirt 314 covering part of the vacuum test tube 390. The skirt 314 facilitates the handling of the vacuum test tube 390 with sampler cap 300. It should be understood that the skirt facility may be applied on sampler caps for syringes and capillary tubes as well.

Figure 4:
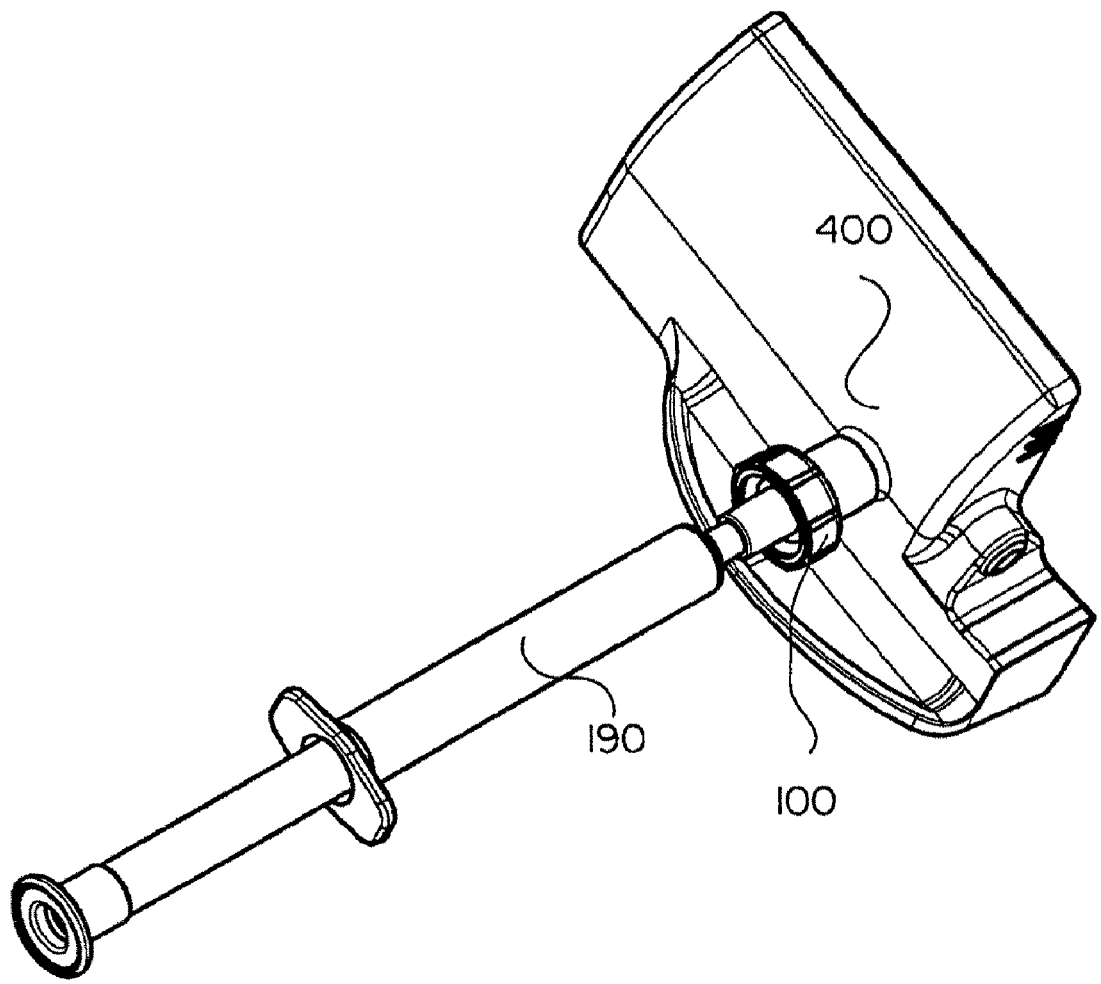
FIG. 4 is a perspective view of the cap of FIG. 1 connected to a syringe and an analyzer inlet.

FIG. 4 shows an example of the syringe 190 with the sampler cap 100 of FIG. 1 engaging with an analyzer inlet 400. The sampler cap 100 fits onto the analyzer inlet 400.

Figure 5A:
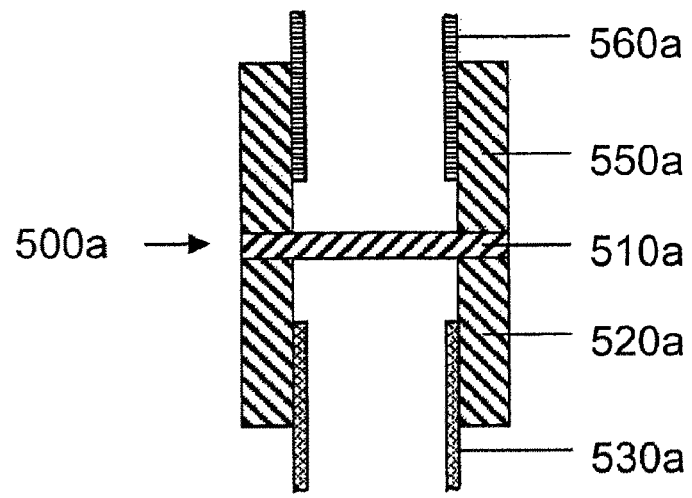
FIG. 5a is a schematic view of a sampler cap with a sampler connector, an analyzer connector and a closure member.

FIG. 5a is a schematic view of a sampler cap 500a with a sampler connector 520a, an analyzer connector 550a and a closure member 510a between the sampler connector 520a and the analyzer connector 550a. The sampler connector 520a engages with a tip 530a of a syringe, and the analyzer connector 550a engages with an analyzer inlet 560a. The design of the sampler cap 500a may be as described above and shown in the other Figures.

Figure 5B:
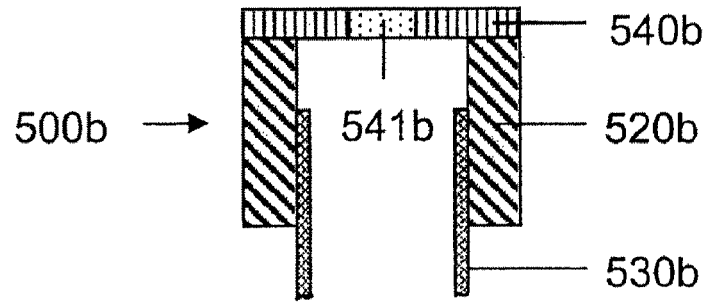
FIG. 5b is a schematic view of a sampler cap with a sampler connector and a liquid impermeable filter with a weakening zone.

FIG. 5b is a schematic view of a sampler cap 500b with a sampler connector 520b and a liquid impermeable filter 540b with a weakening zone 541b. The sampler connector 520b engages with a tip 530b of a syringe. No analyzer connector is required for this embodiment of the sampler cap. The design of the sampler cap 500b may correspond to the design of the sampler caps described above and shown in the other Figures.

Figure 5C:
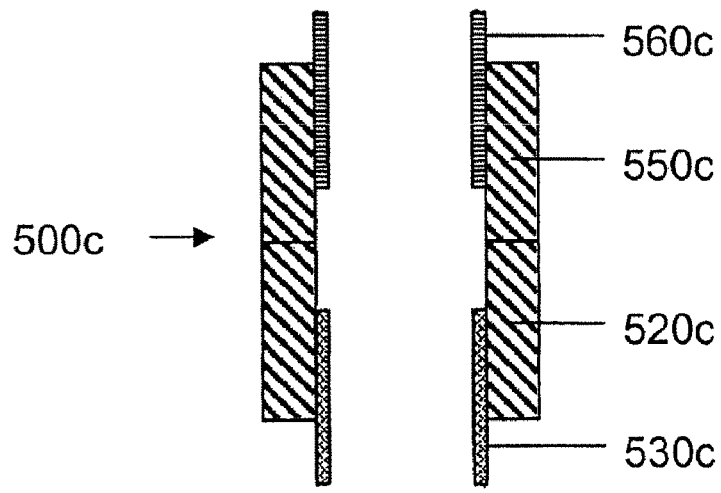
FIG. 5c is a schematic view of a sampler cap with a sampler connector and an analyzer connector.

FIG. 5c is a schematic view of a sampler cap 500c with a sampler connector 520c and an analyzer connector 550c. The sampler connector 520c engages with a tip 530c of a syringe, and the analyzer connector 550c engages with an analyzer inlet 560c. No closure member is required for this embodiment of the sampler cap. The design of the sampler cap 500c may correspond to the design of the sampler caps described above and shown in the other Figures.

Figure 6:
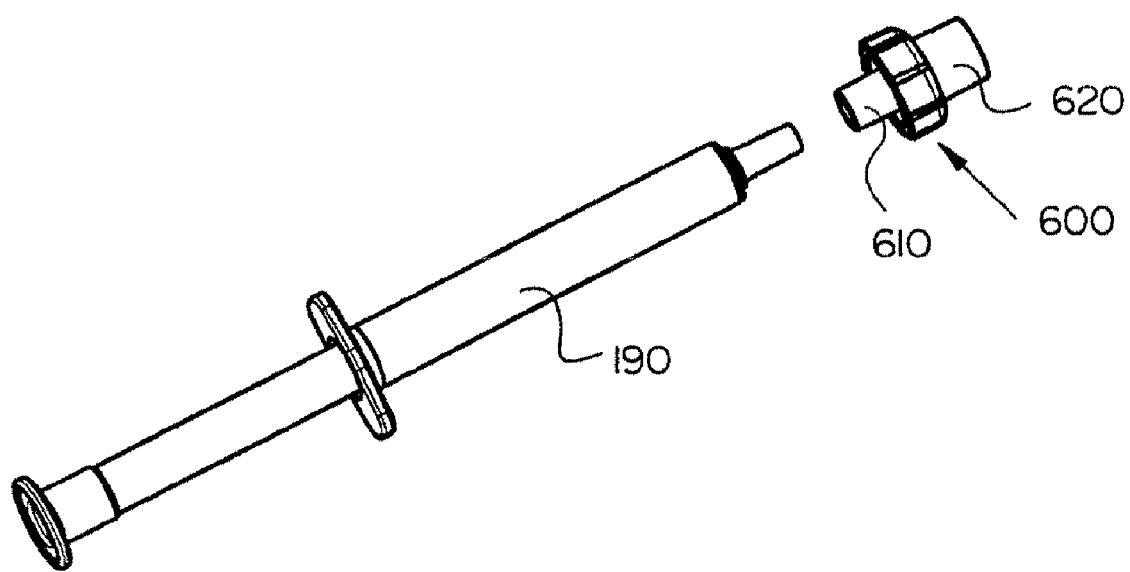
FIG. 6 is a perspective view of a sampler-sampler cap assembly.

FIG. 6 shows a sampler-sampler cap assembly comprising the syringe 190 with a sampler cap 600 comprising a sampler connector 610 and an analyzer connector 620.

Figure 7:
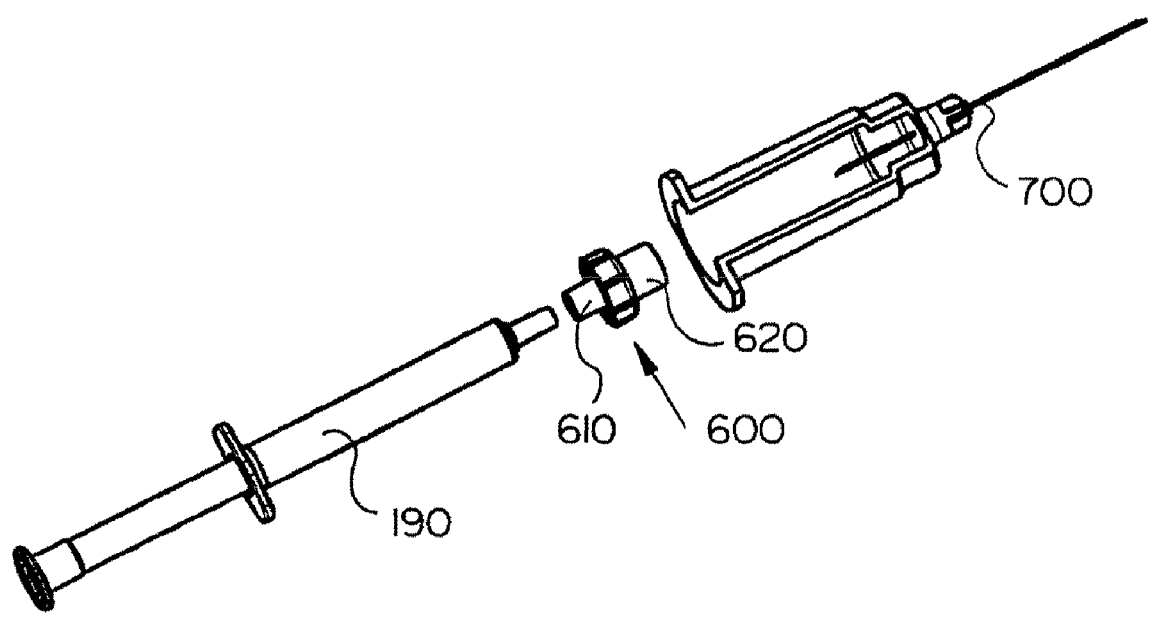
FIG. 7 is a perspective view of a sampler/sampler cap/double-ended needle assembly.

With reference to FIG. 7 is shown the sampler-sampler cap assembly of FIG. 6 combined with a double-ended needle 700.

It will be apparent to those skilled in the art that various modifications and variations can be made in the method and system of the present invention without departing from the spirit or scope of the invention. Thus, it is intended that the present invention cover the modifications and variations of this invention provided they come within the scope of the appended claims and their equivalents.

The invention claimed is:

1. A method of transferring a test sample from a sampler to an analyzer, the sampler being closed with a cap having an analyzer connector, the method comprising:
   venting through the cap the test sample contained in the sampler,
   bringing the sampler closed with the cap into fluid communication with the analyzer by connecting the analyzer connector to an inlet of the analyzer,
   entering an inlet probe of the analyzer into the closed sampler through the cap maintained on the sampler,
   collecting the test sample from the sampler through the inlet probe, and
   retracting the inlet probe from the sampler.

2. The method according to claim 1, wherein the cap further comprises a sampler connector and a liquid impermeable closure member, wherein the sampler connector and analyzer connector together forming at least part of a hollow body and wherein the liquid impermeable closure member intersects the hollow body between the sampler connector and the analyzer connector, wherein the step of entering comprises:
   inserting the inlet probe through the closure member.

3. A method of transferring a test sample from a sampler being closed with a cap to an analyzer, the cap including a hollow body providing a sampler connector having a first open end and a second open end, and a liquid impermeable closure member closing the second end of the sampler connector, the closure member comprising a filter and having a weakening zone, the method comprising:
   venting via the cap the test sample contained in the sampler,
   bringing the sampler closed with the cap into fluid communication with the analyzer by approaching the cap to an inlet of the analyzer,
   entering an inlet probe of the analyzer into the closed sampler through the cap maintained on the sampler,
   collecting the test sample from the sampler through the inlet probe, and
   retracting the inlet probe from the sampler.

\* \* \* \* \*